United States Patent [19]

Masi et al.

[11] 4,405,627
[45] Sep. 20, 1983

[54] DIPHENYLPROPYLAMINO-PYRIDINE COMPOUNDS USEFUL AS MEDICINES

[75] Inventors: Paolo Masi, Bologna; Angela Monopoli, Milan; Adone C. Saravalle, Milan; Cesare Zio, Milan, all of Italy

[73] Assignee: Italiana Schoum S.p.A., Milan, Italy

[21] Appl. No.: 261,296

[22] Filed: May 7, 1981

Related U.S. Application Data

[62] Division of Ser. No. 153,784, May 27, 1980, abandoned.

[30] Foreign Application Priority Data

May 30, 1979 [IT] Italy .............................. 23122 A/79
Mar. 4, 1980 [IT] Italy .............................. 20338 A/80

[51] Int. Cl.³ ........................................... A61K 31/44
[52] U.S. Cl. ................................................. 424/263
[58] Field of Search ........................................ 424/263

[56] References Cited

U.S. PATENT DOCUMENTS 4,180,670 12/1979 Edington et al. .................. 546/284

Primary Examiner—Stanley J. Friedman

[57] ABSTRACT

Novel diphenylpropylamino-pyridine derivatives of general formula:

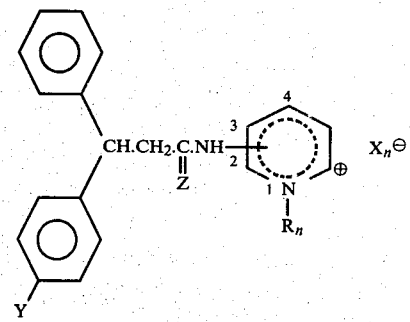

are described and the spasmolytic, miorelaxing and local in vitro and in vivo anesthetic properties of some of them are given on the basis of experimental data as resulting from tests carried out on animals and isolated organs. The synthetized and tested compounds, which are endowed with a low toxicity, reduce the spontaneous motility and the drug-induced contractions, without anticholinergic side-effects at a central level.

5 Claims, No Drawings

DIPHENYLPROPYLAMINO-PYRIDINE COMPOUNDS USEFUL AS MEDICINES

This is a division of application Ser. No. 153,784, filed May 27, 1980, now abandoned.

BACKGROUND OF THE INVENTION

The present invention relates to a series of novel diphenylpropylamino-pyridine compounds which are analogs of phenpyramine and endowed with spasmolytic and miorelaxing activity affecting the smooth muscular system, as well as with local anesthetic activity.

More particularly the present invention relates to a series of novel drugs having the structural general formula:

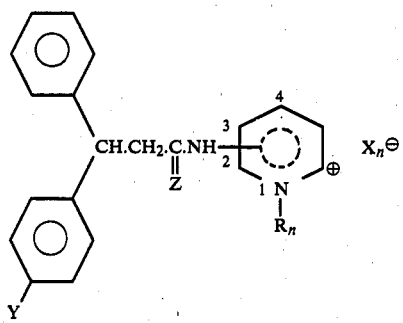

in which the diphenylpropylamine group is bound to the position 2, 3 or 4 of pyridine ring; R can be hydrogen or a low linear or branched chain alkyl group having 1 to 4 carbon atoms or an arylalkyl group such as for instance the benzyl group; X can be a halogen selected from the group consisting of Cl, Br and I; Y is hydrogen or a halogen such as fluorine, bromine and chlorine or also a methoxy group; Z is O or $H_2$; and n can be zero or 1, with the proviso that Z is $H_2$ when n is 1.

Among the compounds comprised in the above general formula, that one in which Y=H, Z=$H_2$, n=zero and NH is bound in position 4, currently named fenpyramine, is known from specialized literature.

The novel compounds according to the present invention can be prepared by the original preparation process of fenpyramine as described in U.S. patent application No. 111,468 filed on Jan. 11, 1980 (now abandoned) in the name of same applicants, which is herein incorporated by reference.

It is known that those drugs wich are endowed to a larger or lesser extent with a spasmolytic activity are mainly formed by the so-called neurotrope drugs, since their action comes out at the synthetic or gangliar level of afferent autonomic nervous system, so that the spasmolytic action is generally part of a set of collateral actions affecting various body organs and districts. Thus for instance the atropinic drugs making up the best known spasmolityc agents of natural origin have side effects both on the autonomic nervous system thereby affecting organs having a parasympathetic innervation (heart, eyes, exocrine glands), and on central nervous system with a global action which is not always foreseable and sometimes paradoxical. The non-desired activity of atropinic drugs is regarded to be due to an antagonistic selective action on muscarinic receptors, which is on the other hand necessary to the accomplishment of the spasmolytic activity.

It is therefore obvious that the variety of non-desired side effects owned by these alkaloids is a drawback when their spasmolytic action has to be therapeutically exploited.

On the other hand papaverine, which is the base element of papaverinic drugs, also named miotropic spasmolytic drugs as they act directly on the smooth muscular system, unlike the antimuscarinic ones whose action comes out through the cholinergic system, notwithstanding its effectiveness on animals has lost its importance in human therapy, because the relevant therapeutical doses do not have often a functional margin with respect to doses which are regarded as toxic.

In other words, the ideal spasmolytic drug should be endowed with a selective action on hollow smooth-muscled organs and not have side effects extending to other sites. A local anesthetic activity owned by this drug would further improve its therapeutical efficaciousness.

SUMMARY OF THE INVENTION

It has now been found that a class of recently prepared drugs is endowed with a remarkable direct spasmolytic action combined with a local anesthetic activity yet showing a low acute toxicity and a reduced appearance of side effects. Some typical representatives of this class do not show quite any undesirable side effects.

A series of compounds according to the present invention which show to a greater extent the desired pharmacological actions have the structural formula I:

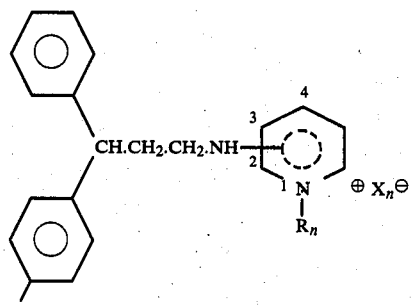

in which R, X and n have the above meaning.

The present invention will now be described in detail based on some embodying examples, which do not have obviously to be construed in a limiting sense.

EXAMPLE 1

Preparation of N-(2'-pyridyl)-3,3-dipenyl-propionamide.

120 g (0.53 moles) of 3,3-diphenyl-propionic acid are suspended in 900 ml of anhydrous benzene and treated with a solution of 44 ml $SOCl_2$ in 150 ml anhydrous benzene. The mixture is heated up to the boiling point and refluxed 8 hours, then the solvent is distilled off and the excess thionyl chloride is removed by sucking out through a suction pump at a temperature of 40°–50° C. The acyl chloride thus obtained is then dissolved in 500 ml dry benzene and treated with a solution of 99.64 g (1.06 moles) of 2-amino-pyridine and heated 8 hours to the boiling point. The solvent is removed under vacuum and the residue is treated with a 15% solution of NaOH and extracted with chloroform.

After the evaporation under vacuum of the solvent, the product is recrystallized from methylene chloride-ethyl ether yielding 120 g of pure product (yield 80%).

Melting point: 126°–128° C.

Chromatography on Kieselgel 60 $F_{254}$ plates with chloroform/ethyl acetate 96/4 as an eluting system: Rf=0.35.

Infrared spectrum (KBr): 3280, 3060, 3020, 1680, 1658, 1598, 1578, 1525, 1492, 1300, 1158, 972, 782, 760, 744, 728, 700 cm$^{-1}$.

Proton Magnetic Resonance (CDCl$_3$): 8.9÷6.5 /(m, 15H, (14H aromatic and NH)/; 4.74 (t,j=8 Hz, 1H); 3.1δ (d,j=8 Hz, 2H).

The compounds given in the following examples were prepared according to the process of Example 1:

EXAMPLE 2

N-(3'-pyridyl)-3,3-diphenylpropionamide.

Yield 74%

Melting point: 236°–238° C.

Chromatography on Kieselgel 60 $F_{254}$ plates with chloroform/methanol 95/5 as an eluting system: Rf=0.41.

IR (KBr): 3430, 3300, 3240, 3175, 3060, 3045, 1690, 1640, 1610, 1585, 1550, 1290, 1195, 815, 760, 750, 730, 705, 697 cm$^{-1}$.

PMR (CF$_3$COOH): 9.5÷7.2/(m, 15H, (14H) aromatic and NH)/, 4.62 (t,J=8 Hz, 1H); 3.45δ (d,J=8 Hz, 2H).

EXAMPLE 3

N-(2'-pyridyl)-3-phenyl-3-p-methoxyphenylpropionamide.

Yield: 80%

Melting point: 108°–110° C.

Chromatography on Kieselgel 60 $F_{254}$ plates with chloroform/methanol 95/5 as the eluting system: Rf=0.29.

IR (KBr): 3290, 3060, 3020, 2950, 2930, 1660, 1610, 1595, 1575, 1525, 1510, 1455, 1430, 1300, 1245, 1180, 1150, 1030, 965, 825, 780, 755, 740, 700 cm$^{-1}$.

PMR (CDCl$_3$): 8.85 (S broadened 1H, NH); 8.30÷6.70 (m, 13H aromatic); 4.62 (t,J=8 Hz, 1H); 3.70 (S, 3H, OCH$_3$); 3.03δ (d,J=8 Hz, 2H).

EXAMPLE 4

N-(2'-pyridyl)3-phenyl-3-p-fluorophenylpropionamide.

Yield: 76%

Melting point: 128°–130° C.

Chromatography on Kieselgel 60 $F_{254}$ plates with chloroform/ethyl acetate 94/6 as the eluent: Rf=0.29.

IR (KBr): 3285, 3060, 3025, 2930, 1665, 1595, 1580, 1530, 1510, 1435, 1295, 1220, 1160, 965, 825, 775, 745, 695 cm$^{-1}$.

PMR (CDCl$_3$): 8.7 (m, 1H, NH); 8.4÷6.6 (m, 13H aromatic); 4.75 (t,j=8 Hz, 1H); 3.1δ (d,J=8 Hz, 2H).

EXAMPLE 5

Preparation of N-(2'-pyridyl)-3,3-diphenylpropylamine.

A solution of 20 g N-(2'-pyridyl)-3,3-diphenylpropionamide in 150 ml dry tetrahydrofurane is slowly added to a suspension of lithium-aluminum hydride (LiAlH$_4$) in excess in 100 ml dry tetrahydrofuran under cooling an ice bath. Once the mixing is ended, the mixture is heated up to the boiling point and refluxed for 4 hours. The LiAlH$_4$ in excess is then resolved with aqueous tetrahydrofurane and the solvent is removed under vacuum. The residue is dissolved with aqueous NaOH 10% and extracted with chloroform. After the solvent is evaporated, the residue is recrystallized from methylene chloride-ethyl ether to give pure N-(2'-pyridyl)-3,3-diphenyl-propylamine with a yield of 77%.

Melting point: 97°–99° C.

Chromatography on Kieselgel 60 $F_{254}$ plates with chloroform/methanol 90/10 as the eluting system: Rf=0.25.

IR (KBr): 3245, 3080, 3050, 3025, 2940, 2920, 2875, 1600, 1575, 1525, 1492, 1485, 1160, 1062, 1030, 983, 770, 750, 740, 698 cm$^{-1}$.

PMR (CDCl$_3$): 8.3÷6.1 (m, 14 H aromatic); 4.75 (m broadened, 1H, NH); 4.07 (t,j=8 Hz, 1H); 3.22 (m, 2H); 2.33δ (m, 2H).

By bubbling gaseous dry HCl through a solution of N-(2'-pyridyl)-3,3-diphenylpropylamine in methylene chloride and by pouring the reaction mixture in ethyl ether, the corresponding hydrochloride having a melting point of 123°–125° C. is obtained.

The following compounds were prepared according to the procedure described in Example 5:

EXAMPLE 6

N-(3'-pyridyl)-3,3-diphenylpropylamine.

Yield: 60%

Melting point: 83°–85° C.

Chromatography on Kieselgel 60 $F_{254}$ plates with chloroform/methanol 95/5 as the eluting system: Rf=0.50.

IR (KBr): 3220, 3020, 1582, 1525, 1490, 1475, 1450, 1420, 1315, 1290, 1250, 1240, 793, 773, 752, 747, 698 cm$^{-1}$.

PMR (CDCl$_3$): 8.1÷6.6 (m, 14 H aromatic); 4.09 (t,j=8 Hz, 1H); 3.7 (m very broadened, 1H, NH); 3.13 (m, 2H), 2.35δ (m, 2H).

The hydrochloride melts at 205°–207° C.

EXAMPLE 7

N-(2'-pyridyl)-3-phenyl-3-p-methoxyphenylpropylamine.

Yield: 75%

Melting point: amorphous product

Chromatography on Kieselgel 60 $F_{254}$ plates with chloroform/methanol 95/5 as the eluting system: Rf=0.18.

IR (KBr): 3250, 3020, 2930, 1600, 1570, 1510, 1440, 1325, 1245, 1175, 1150, 1030, 770, 735, 695 cm$^{-1}$.

PMR (CDCl$_3$): 8.20÷6.10 (m, 13 H aromatic); 4.80 (m, 1H, NH); 4.01 (t,J=8 Hz, 1H); 3.72 (S, 3H, OCH$_3$); 3.20 (m, 2H); 2.31δ (m, 2H).

EXAMPLE 8

N-(2'-pyridyl)-3-phenyl-3-p-fluorophenylpropylamine.

Yield: 70%

Melting point: amorphous product

Chromatography on Kieselgel 60 $F_{254}$ plates with chloroform/ethyl acetate 90/10 as the eluting system: Rf=0.26.

IR (KBr): 3250, 3080, 3020, 2940, 2915, 1600, 1570, 1525, 1505, 1450, 1440, 1330, 1225, 1155, 765, 735, 695 cm$^{-1}$.

PMR (CDCl$_3$): 8.4÷6.2 (m, 13 H aromatic); 4.6 (m, broadened, 1H, NH); 4.07 (t,j=8 Hz, 1H); 3.25 (m, 2H); 2.35δ (m, 2H).

EXAMPLE 9

Preparation of 2-(3',3'-diphenylpropyl-1'-amino)-1-methylpyridinium iodide.

A solution of 5 g N-(2'-pyridyl)-3,3-diphenylpropylamine in 50 ml toluene is treated with an excess of methyl iodide and heated up to the boiling point.

After 3 hours boiling under reflux the reaction mixture is cooled, poured in methyl ether and filtered to give 2-(3',3'-diphenylpropyl-1'-amino)-1-methylpyridinium iodide with a yield of 90%.

IR (KBr): 3220, 3025, 2955, 2935, 1645, 1588, 1538, 1493, 1310, 1185, 1067, 780, 770, 750, 740, 705, 700 cm$^{-1}$.

PMR (CDCl$_3$): 8.2÷6.5 (m, 14H aromatic); 4.1 (s, 3H and, covered, t, 1H); 3.5 (m, 2H); 2.65$\delta$ (m, 2H).

The following compounds were prepared according to the process described in Example 9:

EXAMPLE 10

2-(3',3'-diphenylpropyl-1'-amino)-1-ethylpyridinium iodide.

Yield: 90%

IR (KBr): 3240, 3030, 2935, 1644, 1588, 1535, 1495, 1178, 1158, 768, 750, 700 cm$^{-1}$.

PMR (CDCl$_3$): 8.4÷6.4 (m, 14H aromatic and NH); 4.56 (q,J=7 Hz, 2H); 4.09 (t,j=8 Hz, 1H); 3.52 (m, 2H); 2.55 (m, 2H); 1.45 (t,j=7 Hz, 3H).

EXAMPLE 11

2-(3',3'-diphenylpropyl-1'-amino)-1-benzylpyridinium bromide.

Yield: 97%

IR (KBr): 3180, 3020, 1643, 1580, 1535, 1490, 1450, 1160, 750, 735, 700, 695 cm$^{-1}$.

PMR (CDCl$_3$): 9.1 (m, 1H, NH); 8.2÷6.4 (m, 19H aromatic); 6.1 (d,J=1 Hz, 2H); 3.8 (t,j=8 Hz, 1H); 3.35 (m, 2H); 2.45$\delta$ (m, 2H).

EXAMPLE 12

3-(3',3'-diphenylpropyl-1'-amino)-1-methylpyridinium iodide.

Yield: 80%

IR (KBr): 3230, 3140, 3105, 3065, 1625, 1600, 1545, 1510, 1495, 1470, 1175, 1028, 818, 797, 779, 767, 752, 730, 710, 703, 667 cm$^{-1}$.

EXAMPLE 13

3-(3',3'-diphenylpropyl-1'-amino)-1-ethylpyridinium iodide.

Yield: 85%

IR (KBr): 3222, 3140, 3070, 3020, 2980, 2940, 2920, 2870, 1625, 1600, 1590, 1550, 1510, 1495, 1170, 1155, 1028, 820, 795, 780, 764, 730, 705, 675 cm$^{-1}$.

PMR (CDCl$_3$): 8.7÷7 (m, 15H, (14H aromatic and NH); 4.4 (m, 3H); 3.15 (m, 2H); 2.5 (m, 2H); 1.07$\delta$ (t,j=7 Hz, 3H).

EXAMPLE 14

4-(3',3'-diphenylpropyl-1'-amino)-1-methyl-pyridinium iodide.

Yield: 91%

IR (KBr): 3235, 3135, 3055, 1652, 1560, 837, 817, 785, 752, 747, 710, 695 cm$^{-1}$.

PMR (CDCl$_3$): 8.46 (m, 1H, (NH)); 8.05÷7 (m, 14H aromatic); 4.15 (t,j=8 Hz, 1H); 3.9 (s, 3H); 3.12 (m, 2H); 2.5$\delta$ (m, 2H).

EXAMPLE 15

4-(3',3'-diphenylpropyl-1'-amino)-1-ethyl-pyridinium iodide.

Yield: 87%

IR (KBr): 3250, 3220, 3135, 3030, 1650, 1580, 1555, 1190, 1040, 1030, 830, 810, 780, 752, 746, 710, 698 cm$^{-1}$.

PMR (CDCl$_3$): 8.6 (m, 1H, (NH)); 8.2÷7 (m, 14H aromatic); 4.22 (m, 3H); 3.21 (m, 2H); 2.51 (m, 2H); 1.41$\delta$ (t,j=7 Hz, 3H).

Some of the synthetized compounds have been submitted to a pharmacological test according to the hereinafter described procedures and with the results as shown in the tables and discussed hereinafter. Also the following examples are of course given for explanatory and non-limiting purposes.

The examined compounds in the form of hydrochlorides were tested, as far as the spasmolytic and miorelaxing activity both in vitro and in vivo is concerned, with particular reference to papaverine and the relevant effects were pointed out both on the basis of spontaneous motility and of excitation as induced on insulation viscera by means of some spasmogenic agents (BaCl$_2$, acetylcholine), by using for each test the most convenient preparations. For those doses at which some of the examined compounds are little soluble dimethylsulfoxide was used as a solvent at concentrations which turned out inactive on the considered preparations.

At last in order to determine the dose required to have a 50% reduction of the amplitude of contractions with respect to the starting one (CI$_{50}$) equimolar concentrations of each substance were used.

SPASMOLYTIC AND MIORELAXING ACTIVITY IN VITRO

EXAMPLE 16

Spontaneous motility of rabbit ileum

The action of the examined substances on spontaneous motility was evaluated on 6 rabbit ileum preparations according to the procedure of Magnus (Arch. Ges. Physiol. 102, 123, 1904).

The ileum segments were drawn from New Zealand male rabbits weighing 2.5 kg, suspended in baths for isolated organs containing a buffer saline currently known as Tyrode, which was maintained at 37° C., and lastely oxygenated with a mixture O$_2$—CO$_2$ (95%–5%). The spontaneous motility of the preparations was measured by a isotonic transducer connected with a microdynamometer. Each preparation was previously left dipped for about one hour in the solution up to reach the osmotic equilibrium.

After this time the single compounds were poured in the bath in gradual doses up to notice the quite total disappearance of spontaneous activity in the organ. For sake of comparison parallel tests with papaverine were carried out.

The CI$_{50}$ values which express the necessary concentration to have a 50% reduction of amplitude of the basal contraction are shown in table 1.

(A typical composition of Tyrode is as follows: NaCl 136.9 mmol l$^{-1}$; KCl 2.68 mmol l$^{-1}$; MgCl$_2$ 1.05 mmol l$^{-1}$; CaCl$_2$ 1.80 mmol l$^{-1}$; NaH$_2$PO$_4$ 0.42 mmol l$^{-1}$; NaHCO$_3$ 11.9 mmol l$^{-1}$; glucose 5.56 mmol l$^{-1}$).

TABLE 1

Spontaneous motility in vitro of rabbit ileum

| Compounds | $CI_{50}$ (Mole/l) |
|---|---|
| N—(2'-pyridyl)-3,3-diphenylpropylamine hydrochloride | $1.3 \times 10^{-5}$ |
| N—(3'-pyridyl)-3,3-diphenylpropylamine hydrochloride | $1.2 \times 10^{-5}$ |
| 4-(3',3'-diphenylpropyl-1'-amino)-1-methylpyridinium iodide | $1.8 \times 10^{-5}$ |
| 4-(3',3'-diphenylpropyl-1'-amino)-1-ethylpyridinium iodide | $2.4 \times 10^{-5}$ |
| 3-(3',3'-diphenylpropyl-1-amino)-1-methylpyridinium iodide | $1.5 \times 10^{-5}$ |
| 3-(3',3'-diphenylpropyl-1'-amino)-1-ethylpyridinium iodide | $1.6 \times 10^{-5}$ |
| 2-(3',3'-diphenylpropyl-1'-amino)-1-methylpyridinium iodide | $2.6 \times 10^{-5}$ |
| 2-(3',3'-diphenylpropyl-1'-amino)-1-ethylpyridinium iodide | $1.8 \times 10^{-5}$ |
| Papaverine hydrochloride | $3.9 \times 10^{-5}$ |

From table 1 it can be noticed that all of the examined compounds are effective in checking the spontaneous movements of rabbit ileum at lower concentrations than papaverine.

EXAMPLE 17

In vitro action on rabbit ileum stimulated with $BaCl_2$

The activity of same compounds in antagonizing the spasm as caused by $BaCl_2$ introduced in the bath at a concentration of 50 mcg/ml one minute before each test was studied. Also for this preparation a comparison with papaverine was at last carried out.

The $CI_{50}$ values which express the necessary concentration to have a 50% reduction of the $BaCl_2$-induced contraction are given for each compound in table 2.

TABLE 2

$BaCl_2$—induced contraction on isolated rabbit ileum

| Compounds | $CI_{50}$ (Mole/l) |
|---|---|
| N—(2'-pyridyl)-3,3-diphenylpropylamine hydrochloride | $1.4 \times 10^{-5}$ |
| N—(3'-pyridyl)-3,3-diphenylpropylamine hydrochloride | $2.8 \times 10^{-5}$ |
| 4-(3',3'-diphenylpropyl-1'-amino)-1-methylpyridinium iodide | $1.4 \times 10^{-5}$ |
| 4-(3',3'-diphenylpropyl-1'-amino)-1-ethylpyridinium iodide | $2.2 \times 10^{-5}$ |
| 3-(3',3'-diphenylpropyl-1'-amino)1-methylpyridinium iodide | $1.4 \times 10^{-5}$ |
| 3-(3',3'-diphenylpropyl-1'-amino)-1-ethylpyridinium iodide | $3.5 \times 10^{-5}$ |
| 2-(3',3'-diphenylpropyl-1'-amino)1-methylpyridinium iodide | $1.0 \times 10^{-5}$ |
| Papaverine hydrochloride | $5.6 \times 10^{-5}$ |

From this table it is noticed that all of the compounds inhibit the $BaCl_2$-induced contraction at lower concentrations than papaverine does.

EXAMPLE 18

In vitro checking of $BaCl_2$-and acetylcholine-induced spasm in guinea pig ileum On the guinea pig ileum, which has a minimum intrinsic motility but a remarkable sensibility to agents causing a contracture or a relaxation of the intestinal smooth muscular system, it was possible to further evaluate the spasmolytic activity of the examined substances. As spasmogenic agents acetylcholine and $BaCl_2$ were used which were respectively added to the bath at final concentrations of 0.1 mcg/ml and 50 mcg/ml.

Ten preparations of guinea pig ileum for each compound were prepared, yet maintaining the same dose range which was used on rabbit ileum.

Whitish female guinea pigs weighing 400-500 g were killed by means of cranial injury, the ileum segments were drawn, dipped in baths for isolated organs containing a Tyrode solution at 37° C. and oxygenated with a mixture $O_2$—$CO_2$ (95%-5%). The contractions were measured by means of an isotonic transducer connected with a microdynamometer. Each preparation was left dipped for about 30 minutes up to reach the equilibrium.

After this time, the single doses of each substance to be examined were introduced three minutes before the spasmogenic substance which was contacted with the preparation for 1 minute. Before the subsequent dose of drug was introduced, the tested organ was allowed to recover the basal conditions and this was ascertained by using the only spasmogenic substance. The process was repeated for all the other concentrations. Afterwards the comparison with the reference spasmolytic substance having a known activity, namely papaverine, was carried out yet working in the same conditions and according to the same procedure.

The $CI_{50}$ values are given in table 3 and 4.

TABLE 3

$BaCl_2$—induced contraction on guinea pig ileum in vitro

| Compounds | $CI_{50}$ (Mole/l) |
|---|---|
| N—(2'-pyridyl)-3,3-diphenylpropylamine hydrochloride | $5.6 \times 10^{-6}$ |
| N—(3'-pyridyl)-3,3-diphenylpropylamine hydrochloride | $6.7 \times 10^{-6}$ |
| 4-(3',3'-diphenylpropyl-1'-amino)-1-ethyl-pyridinium iodide | $8.9 \times 10^{-6}$ |
| 2-(3',3'-diphenylpropyl-1'-amino)-1-methyl-pyridinium iodide | $4.3 \times 10^{-6}$ |
| 2-(3',3'-diphenylpropyl-1'-amino)-1-ethyl-pyridinium iodide | $3.4 \times 10^{-6}$ |
| Papaverine hydrochloride | $9.2 \times 10^{-6}$ |

TABLE 4

Acetylcholine-induced contraction on guinea pig ileum in vitro

| Compounds | $CI_{50}$ (Mole/l) |
|---|---|
| N—(2'-pyridyl)-3,3-diphenylpropylamine hydrochloride | $1.1 \times 10^{-5}$ |
| N—(3'-pyridyl)-3,3-diphenylpropylamine hydrochloride | $1.0 \times 10^{-5}$ |
| 4-(3',3'-diphenylpropyl-1'-amino)-1-methyl-pyridinium iodide | $1.6 \times 10^{-5}$ |
| 4-(3',3'-diphenylpropyl-1'-amino)-1-ethyl-pyridinium iodide | $1.0 \times 10^{-5}$ |
| 3-(3',3'-diphenylpropyl-1'-amino)-1-methyl-pyridinium iodide | $1.7 \times 10^{-5}$ |
| 3-(3',3'-diphenylpropyl-1'-amino)-1-ethyl-pyridinium iodide | $1.2 \times 10^{-5}$ |
| 2-(3',3'-diphenylpropyl-1'-amino)-1-methyl-pyridinium iodide | $0.46 \times 10^{-5}$ |
| 2-(3',3'-diphenylpropyl-1'-amino)-1-ethyl-pyridinium iodide | $0.62 \times 10^{-5}$ |
| Papaverine hydrochloride | $0.85 \times 10^{-5}$ |

The above tables show that all of the examined compounds are effective in checking the $BaCl_2$- and acetylcholine-induced contraction.

SPASMOLYTIC ACTIVITY IN VIVO

The investigation on in vivo spasmolytic activity of the examined compounds was carried out by determining the progress of a vegetable charcoal bolus in rat bowl according to the procedure of Loewe (J. Am. Pharm. Ass. 28, 427, 1939).

EXAMPLE 19

Effect on intestinal progress

Male Wistar rats weighing 150-180 g were employed subdivided in groups of ten subjects, which were maintained fasting for 18 hours before the test.

Two administration ways were considered: oral and intraperitoneal.

In the first set of tests to every group of animals each compound was orally administered in the form of an aqueous solution or suspension in gum-arabic (10% in water) 40 minutes before an opaque meal consisting of a suspension of 5% vegetable charcoal in gum-arabic (20% in water).

The animals were killed by cranial injury 40 minutes after the oral administration of the opaque meal and the small intestine was drawn. To the control group an equal volume of saline was administered in the same administration way. The second set of tests was carried out by administering intraperitoneally the compounds 30 minutes before the opaque meal. The animals were killed 40 minutes after the swallowing of the alimentary bolus and the small intestine was drawn; to the control group an equal volume of saline was injected. The total length of small intestine and the progress of opaque meal were measured in each killed animal.

Table 5 shows the values corresponding to the percentage of progress of alimentary bolus 40 minutes after swallowing with respect to the total length of small intestine, as obtained from the mean of ten measures with the relevant standard errors.

TABLE 5

Effect on the intestinal progress of opaque meal in rat

| Compounds | Dose (mg/kg) | Administration way | Progress % |
|---|---|---|---|
| CONTROLS | — | — | 81.76 ± 2.33 |
| N—(2'-pyridyl)-3,3-diphenyl-propylamine hydrochloride | 50 | os | 67.65 ± 2.54 |
| N—(2'-pyridyl)-3,3-diphenyl-propylamine hydrochloride | 20 | i.p. | 62.10 ± 2.54 |
| N—(3'-pyridyl)-3,3-diphenyl-propylamine hydrochloride | 100 | os | 79.10 ± 5.3 |
| N—(3'-pyridyl)-3,3-diphenyl-propylamine hydrochloride | 20 | i.p. | 75.06 ± 5.94 |
| 2-(3',3'-diphenylpropyl-1'-amino)-methylpyridinium iodide | 100 | os | 73.63 ± 4.33 |
| Papaverine hydrochloride | 200 | os | 70.2 ± 2.61 |

From this table it comes out that N-(2'-pyridyl)-3,3-diphenylpropylamine hydrochloride is the most active compound in reducing the progress of an opaque meal in both of the considered administration ways.

EXAMPLE 20

Effect on carbachol-stimulated intestinal motility

Subsequently a further series of tests were carried out in order to evaluate the capability of some examined compounds in hindering the stimulating action on intestinal motility of a dose of carbachol at the concentration of 30 mcg/kg when intraperitoneally administered. Carbachol or carbamylcholine chloride is a known substance endowed with parasympathomimetic action.

A procedure according to the previous tests was adopted by intraperitoneally injecting the examined compounds 30 minutes before carbachol and by killing the animals (rats) 20 minutes after the assumption of the opaque meal in order to be sure that the alimentary bolus did not pass into the colon. The control group was given an equal volume of saline.

The survey of the data as given in tables 6 was carried out as previously described by considering the percent intestinal progress of opaque meal with respect to the total length of small intestine.

TABLE 6

Effect on intestinal progress in rats after excitation with carbachol
(Mean of ten measures with relevant standard errors)

| Compounds | Dose (mg/kg) | Administration way | Progress % |
|---|---|---|---|
| NON-STIMULATED CONTROLS | — | — | 55.7 ± 2.23 |
| STIMULATED CONTROLS | — | — | 77.95 ± 1.72 |
| N—(2'-pyridyl)-3,3-diphenyl-propylamine hydrochloride | 40 | i.p. | 42.25 ± 3.34 |
| N—(3'-pyridyl)-3,3-diphenyl-propylamine hydrochloride | 40 | i.p. | 49.85 ± 3.34 |

The table shows that both the examined compounds have a moderate inhibiting activity on the carbachol-stimulated progress of an opaque meal.

CENTRAL AND PERIPHERAL ANTICHOLINERGIC ACTIVITY

In order to evaluate the possible undesirable collateral systemic effects, tests of central and peripheral anticholinergic activity were carried out by using two animal species, mouse and rat.

EXAMPLE 21

In the first series of tests Swiss male mice averaging 25 g were used which were subdivided in three groups of 8 animals. To the first two groups the substance to be examined was intraperitoneally administered 30 minutes before an injection of Tremorin (butynylene-dipyrrolidine, at the dose of 25 mg/kg i.p;) at the respective doses of 50 and 100 mg/kg. The third, control group was given an equal volume of saline.

In watching the effects caused by Tremorin during the development of its action, beside the time for the appearance of tremors as an index of the central activity, further parameters such as ptyalism and miosis were contemplated as indexes of peripheral activity.

TABLE 7

Central and peripheral anticholinergic activity in mouse after administration of Tremorin

| Compounds | Dose (mg/kg) i.p. | Tremors | Ptyalism | Miosis |
|---|---|---|---|---|
| CONTROLS | — | + | + | + |
| N—(2'-pyridyl)-3,3-diphenyl-propylamine hydrochloride | 50 | + | + | + |
| N—(2'-pyridyl)-3,3-diphenyl-propylamine hydrochloride | 100 | + | + | + |
| N—(3'-pyridyl)-3,3-diphenyl-propylamine hydrochloride | 50 | — | + | + |
| N—(3'-pyridyl)-3,3-diphenyl-propylamine hydrochloride | 100 | — | — | — |
| Atropine sulfate | 60 | — | — | — |

+: Presence of the effect (ptyalism, miosis, tremors)
—: Lack of the effect (ptyalism, miosis, tremors).

From this table it is noticed that N-(2'-pyridyl)-3,3-diphenyl-propylamine hydrochloride at the used doses does not antagonize the ffects of Tremorin neither at a central level nor at a peripheral level.

EXAMPLE 22

Another series of experiments was carried out on male Wistar rats averaging 150 g in order to point out the anticholinergic activity at the glandular level.

A first control group consisting of six animals was subcutaneously injected with 160 mcg of acetylcholine. After 3 minutes into the conjunctival sac of each animal a little piece of filtering paper was introduced: the muscarinic effect appeared in the form of a red-brown spot on the paper.

To a second group of rats the substances to be examined were intraperitoneally administered at the previously used doses 30 minutes before the injection of acetylcholine; after 3 minutes the peripheral cholinergic effect was observed as it was described for the controls.

The results of the observations are summarized in table 8.

TABLE 8

Anticholinergic activity on chromodacryorrhea from acetylcholine

| Compounds | Dose (mg/kg) i.p. | Chromodacryorrhea |
|---|---|---|
| CONTROLS | — | + |
| N—(2'-pyridyl)-3,3-diphenyl-propylamine hydrochloride | 50 | + |
| N—(3'-pyridyl)-3,3-diphenyl-porpylamine hydrochloride | 50 | + |
| Atropine sulfate | 1 | — |

+: Presence of the effect (chromodacryorrhea)
—: Lack of the effect (chromodacryorrhea)

This table shows that both N-(2'-pyridyl)-3,3-diphenylpropylamine and N-(3'-pyridyl)-3,3-diphenyl-propilamine in the form of hydrochlorides at the dose of 50 mg/kg do not modify the acetylcholine-induced chromodacryorrhea.

ACUTE TOXICITY (DL$_{50}$)

The determination of the lethal dose to 50% of the animals which were treated with the examined substances was obtained by using male Swiss mice averaging 22 g and by considering two administration ways: oral and intraperitoneal.

EXAMPLE 23

Groups of six animals of each dose were prepared which were kept under observation for 7 days and fasting since the evening before the experience.

During the observation period possible and clear changes in activity and behaviour were controlled by using the Irwin test: a behavioural outline of the treated animals was obtained with respect to other subjects which received reference drugs.

The calculation of acute toxicity was carried out by using the Litchfield and Wilcoxon procedure (J. Pharmac. Exp. Ther. 96, 99, 1949).

The acute toxicity values in mg/kg are given in table 9 in the form of average values with the relevant fiducial limits in comparison with papaverine.

TABLE 9

Acute toxicity (DL$_{50}$) in mouse

| Compounds | DL$_{50}$ (mg/kg) os | DL$_{50}$ (mg/kg) i.p. |
|---|---|---|
| N—(2'-pyridyl)-3,3-diphenyl-propylamine hydrochloride | >1500 | 360(321–403) |
| N—(3'-pyridyl)-3,3-diphenyl-propylamine hydrochloride | >800 | 340(257–449) |
| 2-(3',3'-diphenylpropyl-1'-amino)-methylpyridinium iodide | 350(269–456) | — |
| Papaverine hydrochloride | 315(258–349) | 66(46–95) |

As it can be seen in this table, the examined substances have a poor oral toxicity and a comparatively low intraperitoneal toxicity.

From the foregoing it comes out that the examined derivatives have a moderate miorelaxing and spasmolytic activity and reduce the spontaneous motility and the BaCl$_2$-induced contractions on rabbit ileum at lower concentrations with respect to papaverine.

In particular N-(2'-pyridyl)-3,3-diphenylpropylamine hydrochloride, N-(3'-pyridyl)-3,3-diphenylpropylamine hydrochloride and 2-(3',3'-diphenylpropyl-1'-amino)-1-methylpyridinium iodide appear more active than papaverine also on BaCl$_2$-stimulated guinea pig ileum and are also effective on the acetylcholine-induced contraction.

They are moreover orally and intraperitoneally active "in vivo" at doses anyhow lower than those of papaverine in reducing the spontaneous or carbachol-stimulated progress of the opaque meal.

Furthermore as already mentioned some of the examined compounds have also a local anesthetic activity: such a characteristic does help in their therapeutical effectiveness.

The examined compounds show at the same time a poor acute toxicity both orally and intraperitoneally.

The less toxic compound based on carried out tests was found to be N-(2'-pyridyl)-3,3-diphenylpropylamine hydrochloride, which does not show anticholinergic side effects at a central level also at high doses.

LOCAL ANESTHETIC ACTIVITY

The tests on local anesthetic activity were carried out by using two animal species: rabbit and mouse.

In the first set of experiments the response to the corneal reflex in rabbit after instillation of the substances to be examined into the conjunctival sac was evaluated (J. Bull. Sci. Pharmacol. 30, 580, 1923).

The tested compounds, N-(2'-pyridyl)-3,3-diphenyl-propyl-amine hydrochloride and N-(3'-pyridyl)-3,3-diphenylpropyl-amine hydrochloride, were employed at the maximum dose which was consistent with the total solubility in saline (0.1%) and were compared with a known local anesthetic, lidocaine (0.2%).

In the second set of experiments the response to a painful drive in mouse was evaluated by applying an hemosthatic forceps at the base of the tail 15 minutes after the intradermic injection of the substances (Brit. J. Pharmacol. 11, 104, 1956).

The tested compounds, N-(2'-pyridyl)-3,3-diphenyl-propyl-amine hydrochloride and N-(3'-pyridyl)-3,3-diphenylpropyl-amine hydrochloride, were used at a concentration of 1% and compared with lidocaine (2%).

The results show that the examined substances at the employed concentrations have a local anesthetic activity with respect to both surface and infiltration anesthesia.

Although the present invention was described on the ground of some embodying examples and with particular reference to hydrochloric salts for the pharmacologic use, it is obvious that changes and/or alterations could be made therein without coming out therefore of the protective scope of the invention. Thus for instance beside hydrochloric acid other pharmacologically acceptable acids can be used in salifying the active bases according to the invention.

What we claim is:

1. A method of treating spastic syndromes in the muscular tissues of mammals comprising administering to the mammal a unitary dosage of from about 20 to 100 mg per kilogram of body weight of a compound having the formula:

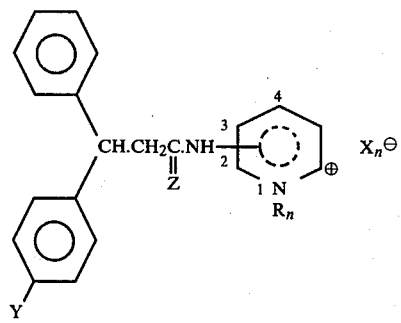

wherein the diphenylpropylamino group is bound at position 2 or 3 of the pyridine ring; R is selected from the group consisting of hydrogen, a lower linear or branched alkyl group having from 1 to 4 carbon atoms and arakyl; X is selected from chlorine, bromine and iodine, Y is selected from hydrogen, fluorine, bromine, chlorine and methoxy; Z is Oxygen or $H_2$ and n is zero or 1, provided that Z is $H_2$ when n is one.

2. A method according to claim 1, wherein the said compound has the following formula:

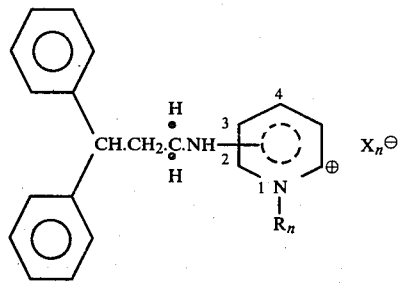

and wherein R, X and n are as therein defined.

3. A method according to claim 1, wherein said compounds is N-(2'-pyridyl)-3,3-diphenylpropylamine.

4. A method according to claim 1, wherein said compound is N-(3'-pyridyl)-3,3-diphenylpropylamine.

5. A method according to claim 1, wherein said compound is 2-(3',3'-diphenylpropyl-1'-amino)-1-methylpyridinium iodide.

* * * * *